(12) United States Patent
Schwieker et al.

(10) Patent No.: US 6,382,832 B1
(45) Date of Patent: May 7, 2002

(54) X-RAY EXAMINATION APPARATUS PROVIDED WITH A TILTABLE PATIENT TABLE

(75) Inventors: Horst Schwieker; Harald Kayser; Heinz Haarmann; Jürgen Rothenstein, all of Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/108,638

(22) Filed: Jul. 1, 1998

(30) Foreign Application Priority Data

Jul. 2, 1997 (DE) .......................................... 197 28 108

(51) Int. Cl.⁷ ................................................. A61B 6/02
(52) U.S. Cl. ........................ 378/196; 378/195; 378/177
(58) Field of Search ................................ 378/195, 196, 378/197, 167, 177, 193

(56) References Cited

U.S. PATENT DOCUMENTS

| | | | | |
|---|---|---|---|---|
| 3,733,487 A | * | 5/1973 | Louche et al. | 378/197 |
| 4,450,575 A | * | 5/1984 | Mueller | 378/197 |
| 4,550,421 A | * | 10/1985 | Louiday | 378/196 |
| 5,497,408 A | * | 3/1996 | Kayser | 378/196 |
| 5,572,567 A | * | 11/1996 | Khutoryasnky et al. | 378/195 |
| 5,636,259 A | * | 6/1997 | Khutoryansky et al. | 378/205 |

OTHER PUBLICATIONS

"Tele Diagnost Remote Control RF System" by Philips, 1998.

* cited by examiner

*Primary Examiner*—David P. Porta
*Assistant Examiner*—Drew A. Dunn
(74) *Attorney, Agent, or Firm*—Dwight H. Renfrew

(57) ABSTRACT

The invention relates to an X-ray examination apparatus which can be universally used for X-ray fluoroscopy and X-ray exposures. It includes a tiltable patient table, a horizontally displaceable stand on which an X-ray source is mounted so as to be vertically displaceable, and a coupling member which couples the stand or the X-ray source to the image converter arrangement provided in the patient table. Depending on the type of coupling, either X-ray fluoroscopy and Bucky exposures or slice exposures are possible. Furthermore, other exposure modes can be performed when the stand is decoupled from the coupling member.

11 Claims, 8 Drawing Sheets

X-RAY EXAMINATION APPARATUS PROVIDED WITH A TILTABLE PATIENT TABLE

All references cited herein, as well as the priority document German Patent Application 19728108.7 filed Jul. 2, 1997, are incorporated herein by reference in their entirety and for all purposes to the same extent as if each individual publication or patent or patent application was specifically and individually indicated to be incorporated by reference in its entirety for all purposes.

BACKGROUND OF THE INVENTION

1. Field of the Invention

The invention relates to an X-ray examination apparatus which includes a patient table which is tiltable about a horizontal axis, an image converter arrangement which is displaceable in the longitudinal direction of the table, and an overtable X-ray source which is aligned with respect thereto.

2. Description of Related Art

X-ray examination apparatus of this kind are known in practice, for example the Philips apparatus "DIAGNOST 120". The X-ray source and the image converter arrangement thereof are accommodated on a carriage which is displaceable in the longitudinal direction of the table. Such an X-ray examination apparatus has a comparatively complex construction and it is suitable for different examination methods to a limited extent only.

Therefore, it is an object of the present invention to construct an X-ray examination apparatus of the kind set forth in such a manner that a simple construction is obtained which nevertheless enables more universal application.

SUMMARY OF THE INVENTION

This object is achieved according to the invention in that the X-ray source is mounted on a horizontally displaceable stand so as to be displaceable in the vertical direction and can be coupled, via a mechanical coupling member, to the patient table in such a manner that upon tilting of the patient table the stand and the X-ray source are displaced in such a manner that the distance between and the alignment of the image converter arrangement and the X-ray source with respect to one another remain the same.

Thus, the X-ray examination apparatus according to the invention includes, in addition to the patient table with the image converter arrangement, which is displaceable in the longitudinal direction of the table, a stand which is slidable in the horizontal direction and on which the X-ray source is mounted so as to be slidable in the vertical direction. The coupling member enables the patient table and the X-ray source to be coupled to one another in such a manner that in response to a tilting motion of the patient table the stand is displaced in the horizontal direction and the X-ray source is displaced in the vertical direction, the distance between and the alignment of the image converter and the X-ray source with respect to one another remaining the same. All customary fluoroscopy methods can be executed by means of such an X-ray apparatus. Moreover, the X-ray examination apparatus according to the invention is also suitable for executing Bucky exposures with a vertical beam path. The displaceability of the stand enables the use of a patient table which is not provided with a "floating" table top but with a table top which is fixed relative to the table frame, resulting in a substantially simpler construction.

When the coupling member is decoupled from the X-ray source, further possibilities arise. In an embodiment, X-ray exposures can be performed by means of the X-ray source on a separate image pick-up device, for example mounted on a Bucky wall stand; the beam path may then extend horizontally and parallel to the direction of displacement of the stand. Another embodiment enables adaptation to different patient sizes. A further embodiment enables X-ray exposures with a beam path extending horizontally and perpendicularly to the longitudinal direction of the table.

Another embodiment offers the above-mentioned examination possibilities in the first mode of operation (rigid coupling between X-ray source and image converter); linear tomography or oblique exposures are possible in the second mode of operation.

The first and the second mode of operation can be implemented by means of the following embodiments. When the carriage supporting the unit for adjusting the slice height is displaced (first mode of operation), the described X-ray fluoroscopy or Bucky exposures are possible. However, when the carriage is blocked relative to the patient table, the X-ray source and the image converter arrangement are displaced in opposite directions. This enables, for example oblique exposures. A preferred embodiment of the invention enables the position of the examination zone to be changed in the first mode of operation and linear tomography to be performed in the second mode of operation.

Yet another embodiment takes into account the fact that the image converter arrangement usually utilizes separate image converters for X-ray fluoroscopy and X-ray exposures. It is thus possible in principle to use an additional carriage for the unit for slice height adjustment.

A preferred embodiment has a construction which is mechanically simpler and also more stable. A further embodiment enables very simple changing over between the two modes of operation. When the two carriages are displaced at the same speed (or when both carriages stand still), X-ray fluoroscopy or Bucky exposures are possible (first mode of operation). When the second drive device has been deactivated and the first drive device acts on the carriage coupled to the coupling member, linear tomography can be performed. A common drive motor can be used for the two drive devices, said motor acting, via a coupling that can be activated and deactivated, on a drive member in the form of, for example a drive spindle.

BRIEF DESCRIPTION OF THE DRAWINGS

The invention will be described in detail hereinafter with reference to the drawings. Therein.

DESCRIPTION OF THE PREFERRED EMBODIMENT

Figure 1:
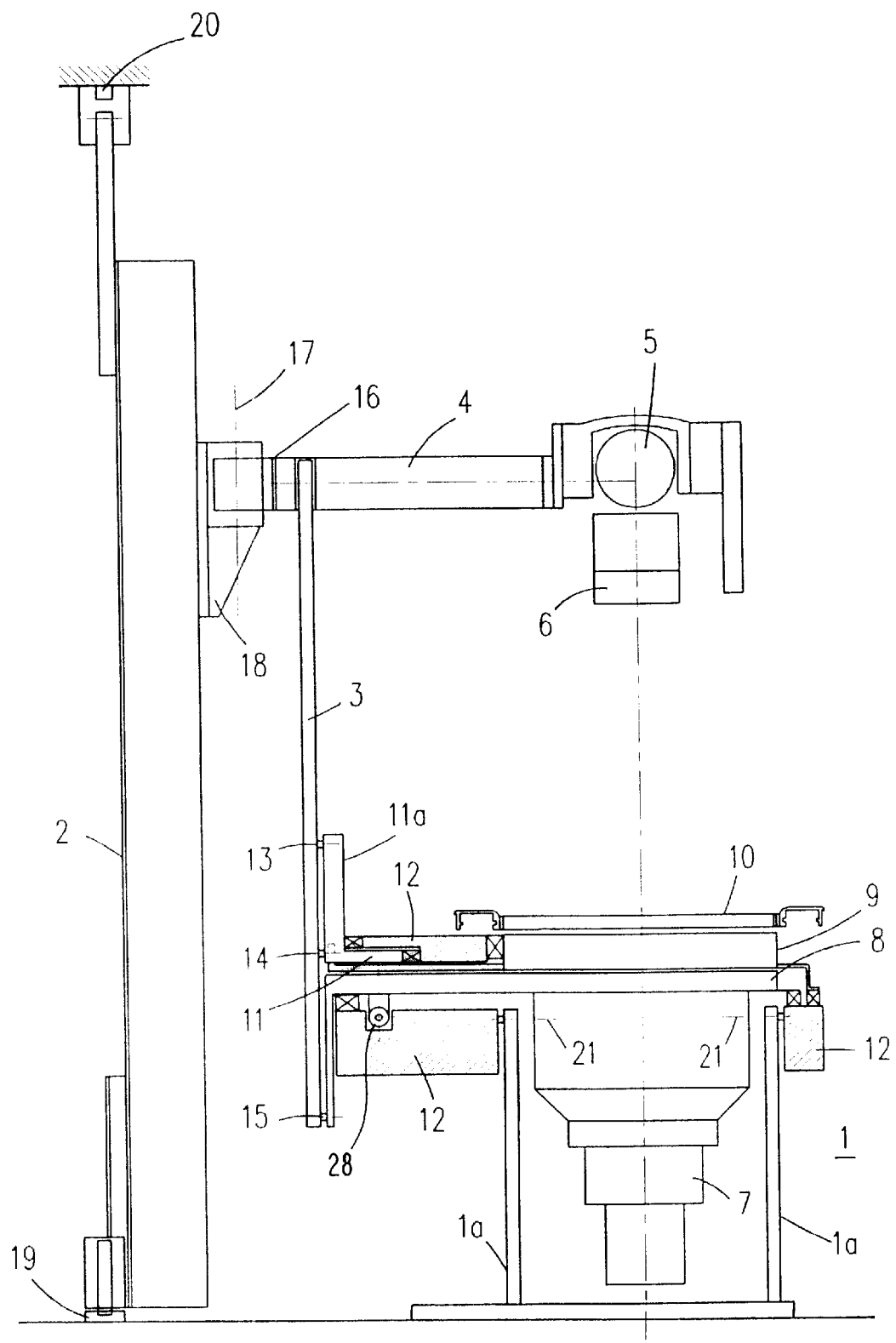
FIG. 1 is a front view of a first embodiment.

The X-ray examination apparatus shown in FIG. 1 has three main components: a patient table 1, a stand 2 and a coupling member 3.

The sleepers 12 of a table frame are mounted on the base 1a (FIG. 2) of the patient table 1 so as to be rotatable about the axis 21. The frame is completed by the crossbars 22 (FIG. 2) which interconnect the sleepers. A table top 10 is mounted on the crossbars 22. Three carriages are displaceable in the longitudinal direction of the sleepers 12: a carriage 8 for an image intensifier 7 for carrying out fluoroscopy, a moving grid carriage 9 for forming X-ray (Bucky) images on a film cassette present therein, and a carriage 11 for a unit 11a for adjusting the slice height which is also referred to hereinafter as slice unit or fulcrum.

The stand 2 is guided on rails 19 and 20 which are provided on the floor and on the ceiling (or a wall) and extend parallel to the longitudinal direction of the table (in the horizontal position of the table top). A carriage 18 is coupled to a counterweight (not shown) and coupled to the stand so as to be displaceable in the vertical direction. An arm 4 of the carriage 18 supports an X-ray source 5 with a multi-leaf collimator 6. The arm 4 is rotatable, by way of a rotary bearing 16, about its (horizontal) longitudinal axis and the rotary bearing 16 itself can pivot on the carriage 18 about a vertical axis 17.

The coupling member 3 couples the arm 4 and the three afore-mentioned carriages in the patient table 1 to one another. The coupling member 3 may be a rod, but other devices providing a mechanically defined coupling between the arm 4 and the carriage are also feasible. The coupling member 3 is connected to the slice unit 11a via a hinge 13 whose height can be adjusted. Furthermore, via the coupling bolts 14 and 15 it is coupled to the carriages 9 and 8 so that these carriages are taken along upon movement of the coupling rod relative to the patient table. These coupling means (11, 11a, 14, 15 and further components) enable the selection of two different modes of operation which will be described in detail hereinafter with reference to the following Figures.

Figure 2:
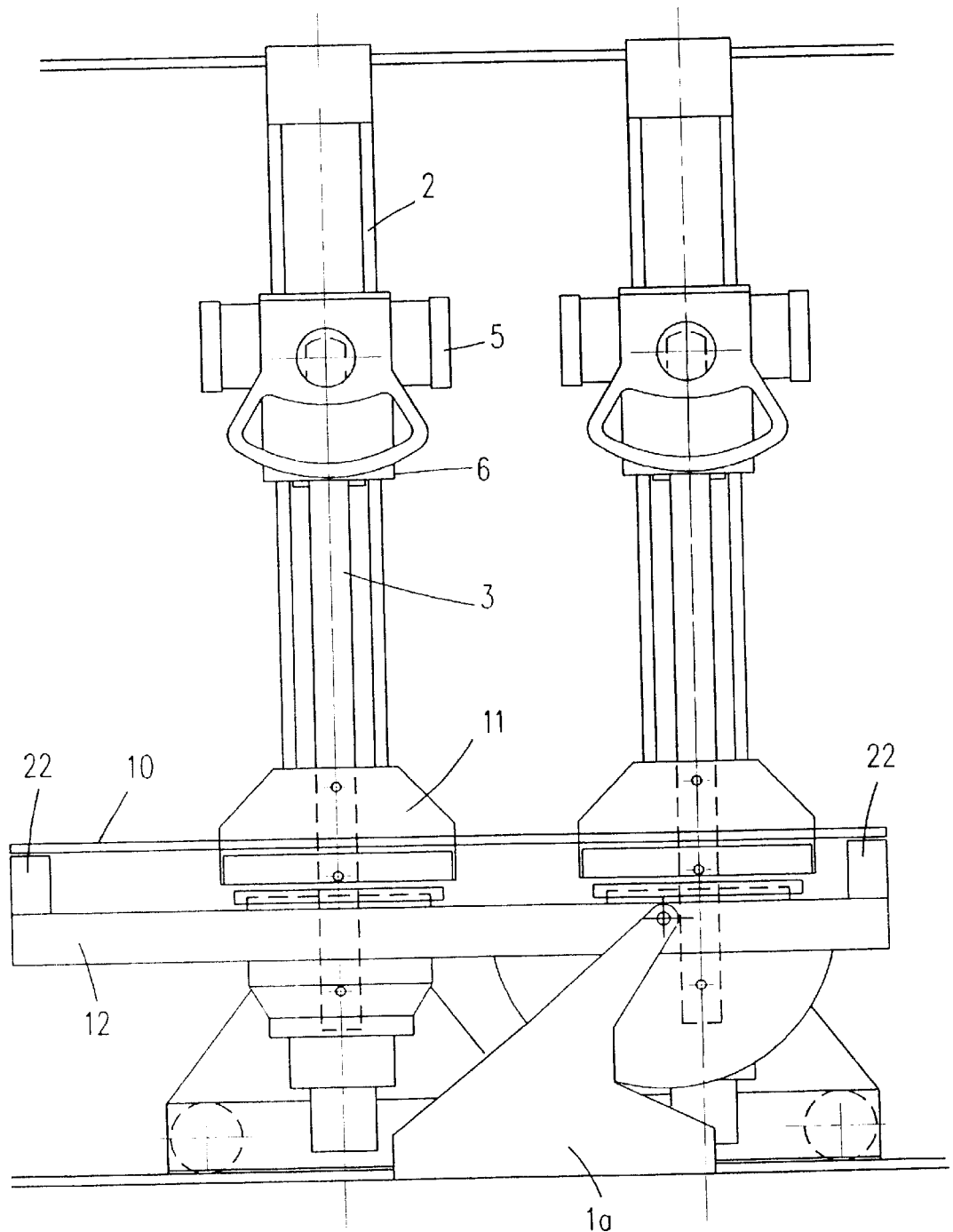
FIG. 2 is a side elevation taken in the Bucky mode.

FIG. 2 shows the X-ray examination apparatus with the table top 10 in a horizontal position in a mode of operation which is suitable for forming Bucky images, the stand being shown in a first and in a second working position. The displacement between these two working positions can be realized by means of a spindle drive 28 (FIG. 1) whereby the carriage 8 and, via the coupling member 3, the carriages 9 and 11 as well as the arm with the stand are displaced. Instead of such a spindle drive, driven by a suitable motor, use can also be made of a chain drive or a toothed rack which co-operates with a gearwheel driven by a motor.

Figure 3:
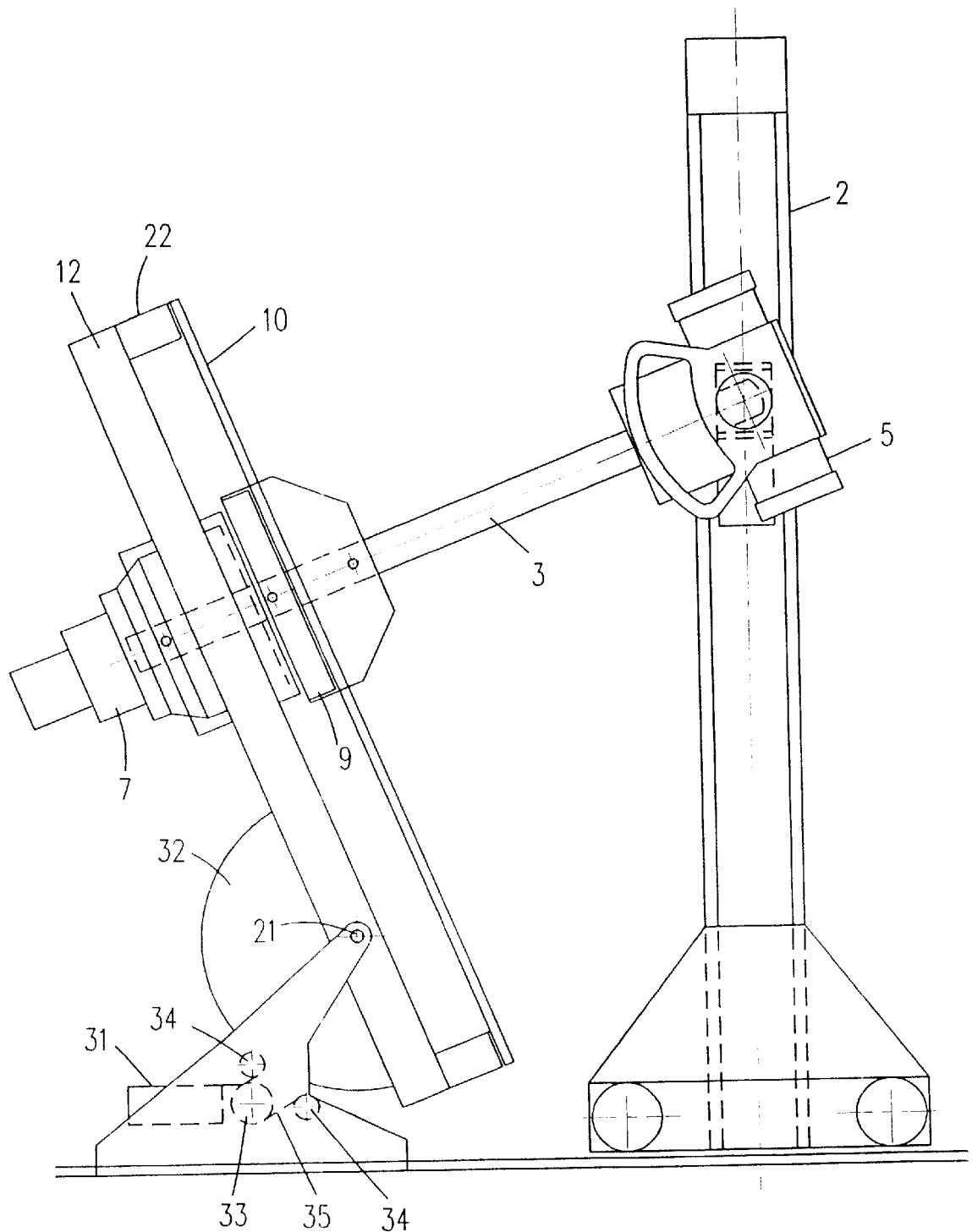
FIG. 3 is a side elevation taken in the fluoroscopy mode.

FIG. 3 shows the X-ray examination apparatus in a working position for X-ray fluoroscopy. The frame 12, 22 and the table top then occupy an inclined position relative to the horizontal. This tilting of the table is performed by means of a drive motor 31 which drives, via a chain 35, a gearwheel 33 and two guide rollers 34, a segment 32 which is connected to the frame 12, 22. In response to a tilting motion, the coupling member 3 causes a displacement of the stand to the right or to the left and at the same time a displacement of the carriage 18 with the X-ray source 5 in the upwards or downwards direction, the distance between and the alignment of the image converter device 7 (or 9) and the X-ray source 5 relative to one another remaining the same. When the carriage 8, and hence also the carriages 9 and 11, is displaced in the longitudinal direction of the table, the X-ray tube is moved along, via the coupling member 3, in such a manner that the distance between and the alignment of the image converter device 7 (or 9) and the X-ray source 5 relative to one another remain the same.

Figure 4:
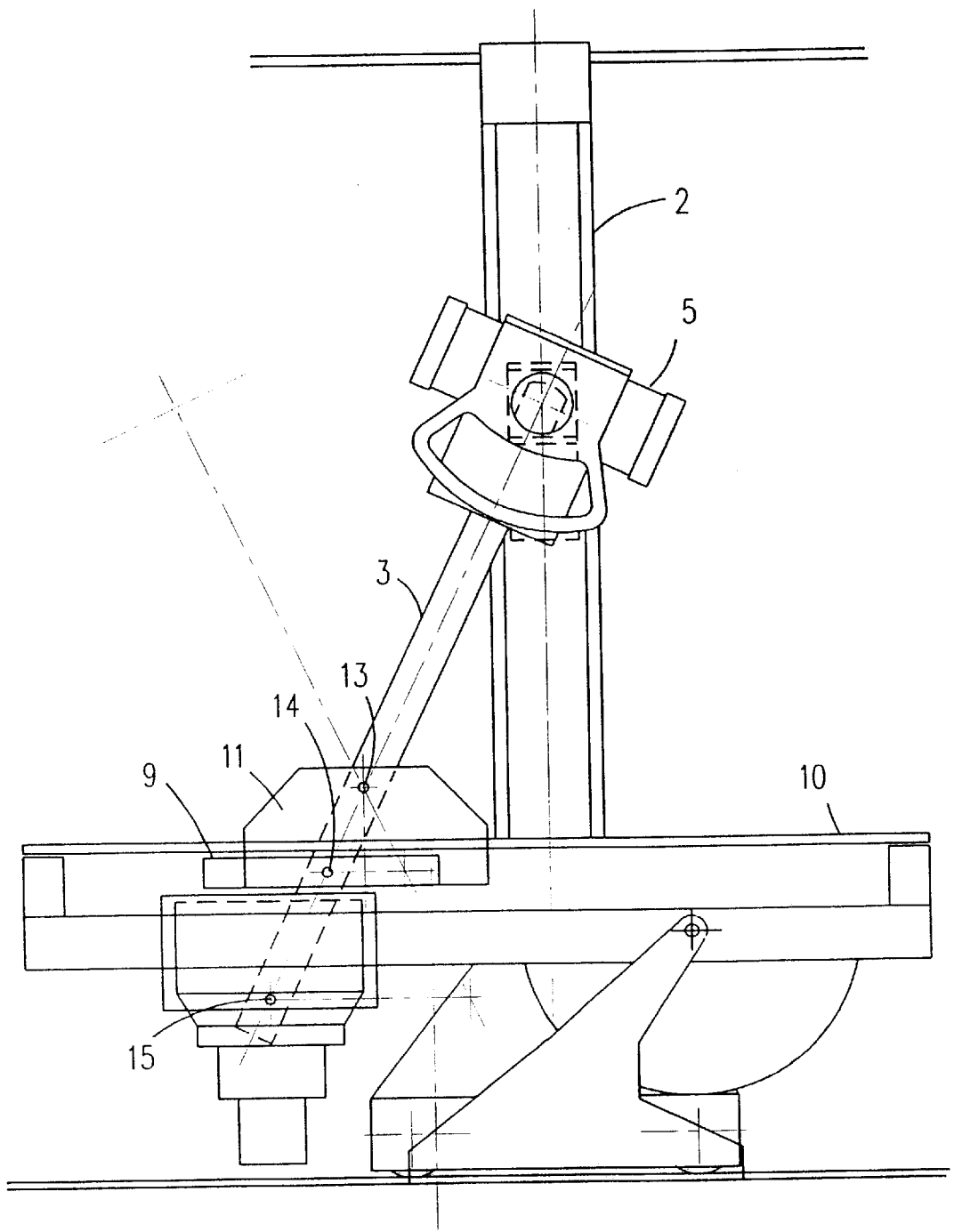
FIG. 4 is a side elevation taken in the case of oblique or slice exposures.

FIG. 4 shows the X-ray examination apparatus with a horizontal table top in a further mode of operation. This mode of operation is obtained when the carriage 11 is locked (for example, by means of a brake or positive locking on the upper sleeper 12) and hence is blocked relative to the patient table. When the carriage 8 with the image intensifier is then displaced, the coupling rod is taken along (via the trunnion 15), the coupling member 3 then being tilted about the locked (immobilized) pivot 15, so that the stand 2 is displaced laterally. The moving grid carriage 9 is taken along, via the trunnions 14, so that an oblique projection is obtained in which the central ray is always aimed at the center of a film cassette provided in the moving grid carriage 9.

When the moving grid carriage 9 is continuously displaced, via the drive 28, in such a manner that the coupling member 3 is moved from its position shown to the position denoted by a dashed line, a slice image with a linear blurring motion (linear tomography) can be formed during this displacement. When the height of the hinge or the coupling point 13 is shifted, the height of the slice sharply imaged during a slice exposure changes accordingly. When the coupling point 13 is moved sufficiently far downwards, oblique fluoroscopy, during which the central ray is incident at the center of the image intensifier 7, is also possible.

Whereas the carriage is fixed on the table 1 during the second mode of operation shown in FIG. 4, the three carriages 8, 9, 11 are rigidly coupled to one another in the first mode of operation as shown in FIG. 2 or FIG. 3, so that when the carriage 8 is displaced, the carriages 9 and 11 are also displaced and take along the stand 2 via the coupling member 3.

Further possibilities arise when the coupling member 3 is decoupled from the arm 4.

Figure 5:
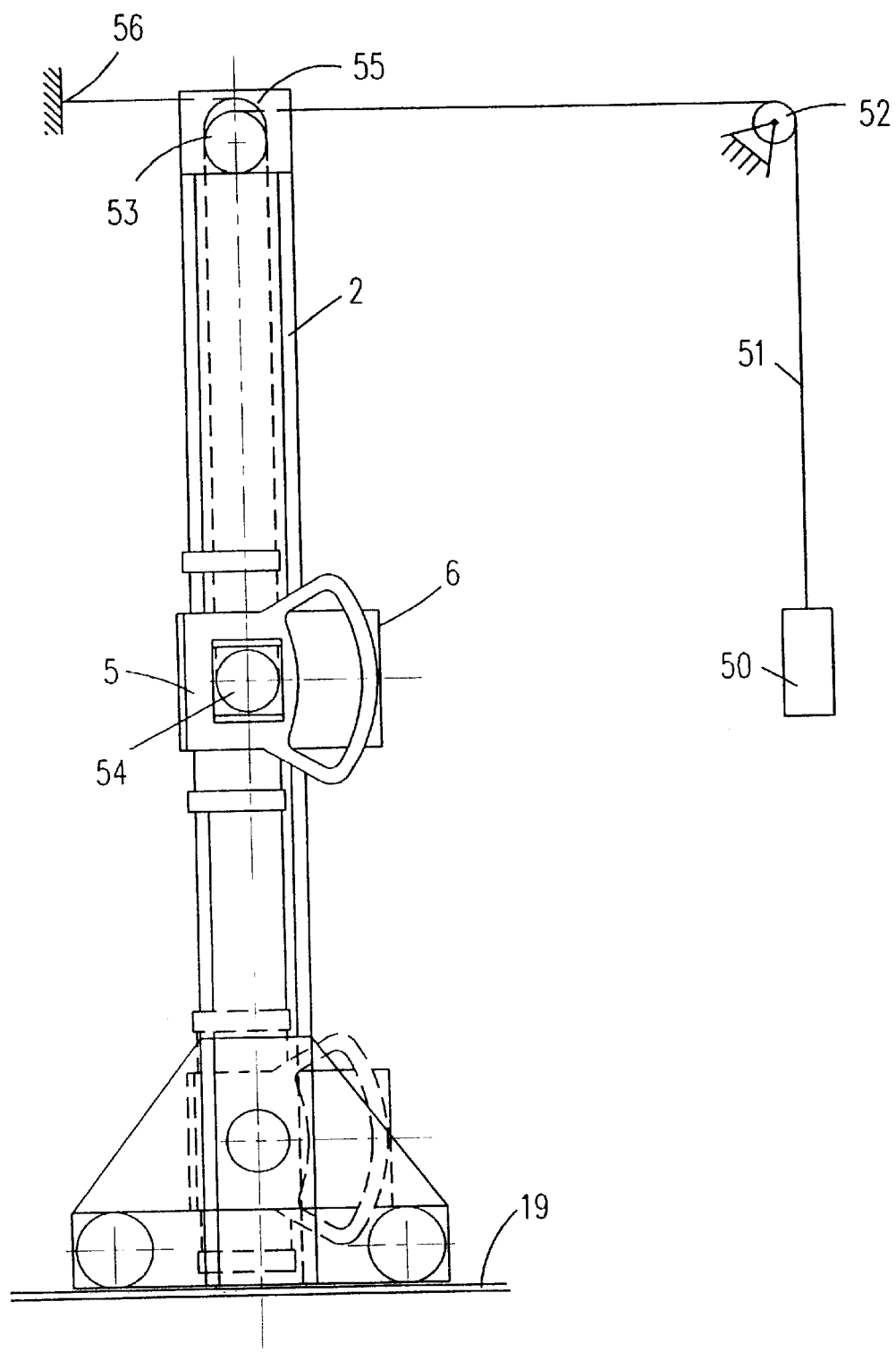
FIG. 5 is a side elevation taken with a horizontal beam path (in the longitudinal direction of the table)

As is shown in FIG. 5, the stand 2 can be displaced beyond the patient table, and the X-ray source 5 can be tilted 90° in the rotary bearing 16 (see FIG. 1), so that lateral exposures can be performed on a wall stand (not shown). Using the carriage 18 (FIG. 1), the X-ray source 5 can then be vertically displaced to arbitrary positions as denoted by dashed lines in FIG. 5.

FIG. 5 also diagrammatically shows the afore-mentioned balancing. It includes a counterweight 50 which balances the weight of the carriage 18, including the arm 4 and the X-ray source 5. If the counterweight 50 were movable within the stand in the opposite direction relative to the X-ray source 5, it would also have to be moved during a displacement of the stand. However, the counterweight is connected to a fixed point 56 via a rope 51 which is guided via a (fixed) roller 52 on the wall or the ceiling, a first roller 53 on the stand 2, a roller 54 on the carriage 18 and a second roller 55 on the stand 2. When this roller arrangement is used, the counterweight can change its position in space only in the vertical direction, but not in the horizontal direction. This offers the advantage that it need not be moved and accelerated upon displacement of the stand 2.

Figure 6:
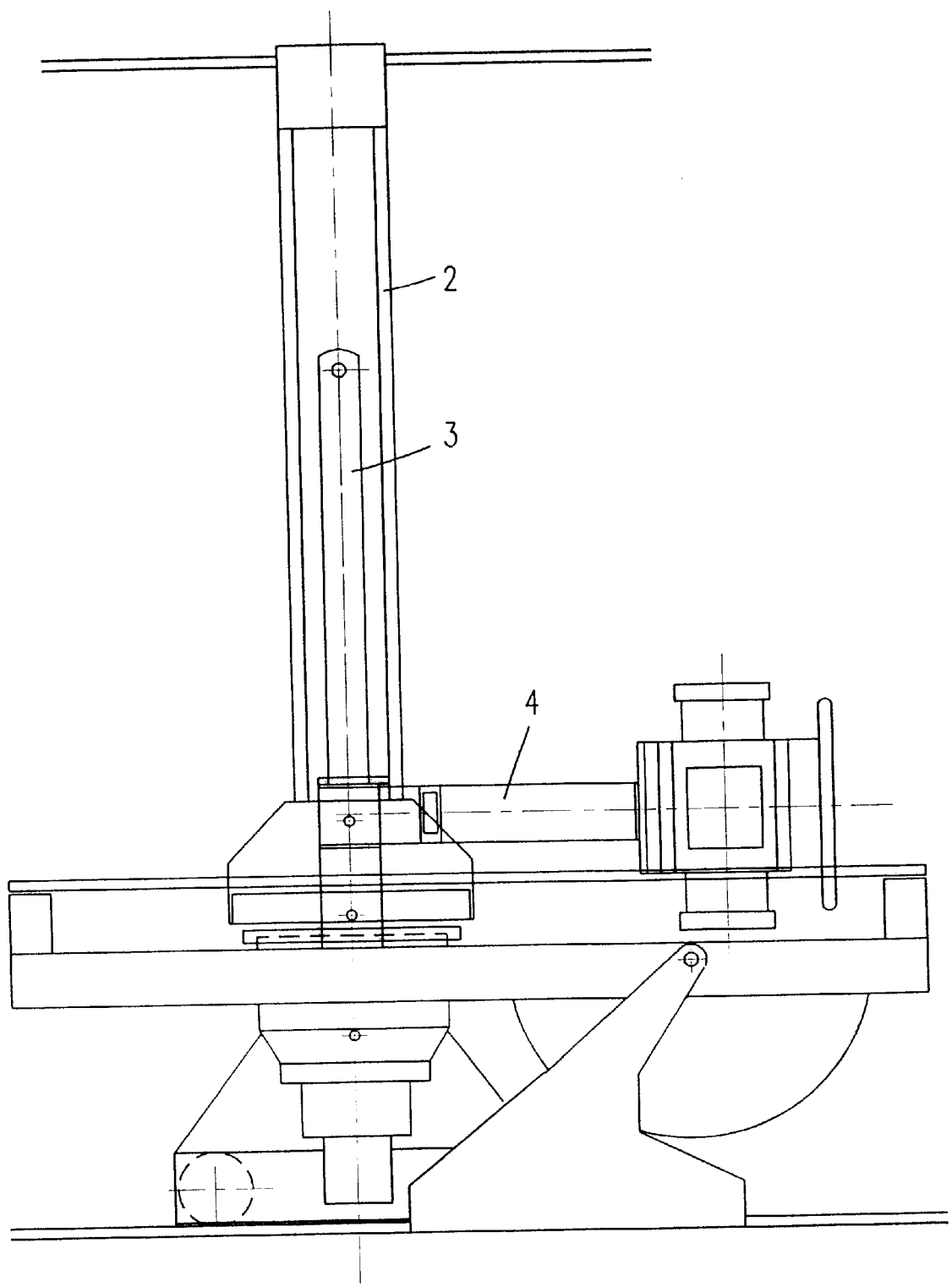
FIG. 6 is a side elevation taken with a horizontal beam path (transversely of the longitudinal direction of the table)

FIG. 6 shows a second possibility for exposure in the decoupled state. This possibility occurs when the arm 4 is tilted about the vertical axis 17 (FIG. 1) and is subsequently rotated 90° about the horizontal axis. A horizontal beam path which extends perpendicularly to the longitudinal direction of the table is then obtained.

Figure 8:
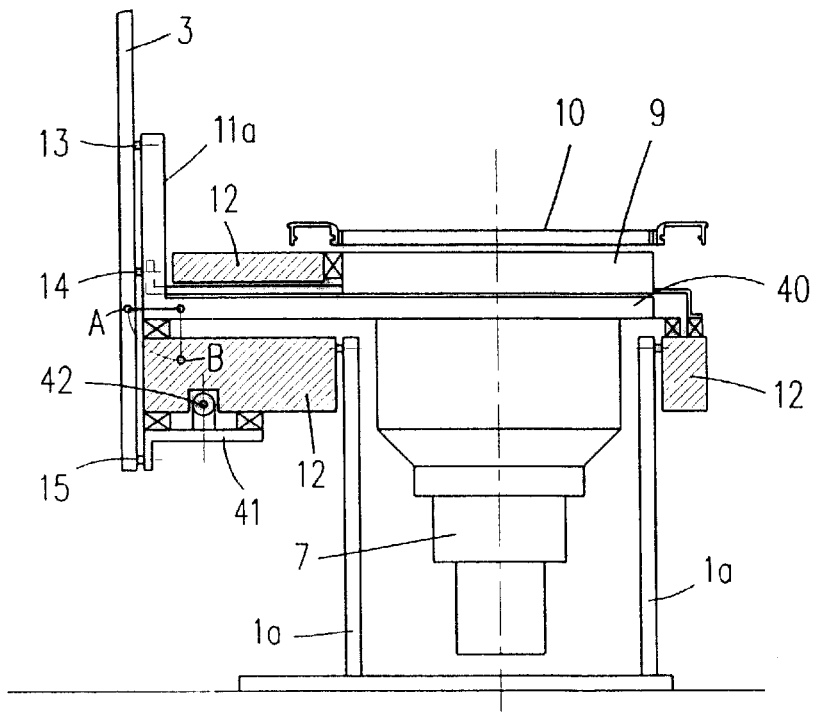
FIG. 8 shows a part of a front view of an improved embodiment.

FIG. 8 is a front view of an improved embodiment of the invention; the Figure shows essentially only the patient table.

Whereas in the embodiment shown in FIG. 1 the slice unit 11a is supported by the carriage 11 and the image intensifier 7 is supported by the separate carriage 8, in the embodiment shown in FIG. 8 a common carriage 40, ensuring more stable guiding of the slice unit, is provided for the slice unit 11a and the image intensifier 7. For the tilting or displacement of the coupling member 3, a drive carriage 41 is provided on the lower side of the left-hand lower sleeper 12, which drive carriage acts on the lower end of the coupling member, via the coupling bolts 15, and is linearly guided in the longitudinal direction of the table. A spindle drive 42 (or a chain drive or the like) acts on the drive carriage 41, the behavior being dependent on whether the carriage 40 is coupled to the coupling member 3 (heavy connection to the point A) or to the sleeper 12 (thin coupling to the point B on the sleeper 12), so that the carriage 40 cannot be displaced.

When the carriage 40 is coupled to the coupling member 3 (at the point A), the carriage 40, the coupling member 3 and the carriage 9 are displaced in the same sense (in the same direction and over the same distance) in conformity with FIG. 2 or FIG. 3 (first mode of operation). When the carriage 40 is coupled to the point B, i.e. fixed relative to the sleeper 12, the drive carriage pivots, via the coupling bolts 15, the coupling member 3 about the hinge 13 in conformity with FIG. 4. It is an advantage that the image intensifier 7 is not moved simultaneously (the carriage 40 is then stationary), so that the drive 42 need not provide acceleration or braking forces for this purpose. This is because the image intensifier 7 is not required for slice exposures.

A further advantage resides in the increased region within which slice exposures can be performed.

Figure 7:
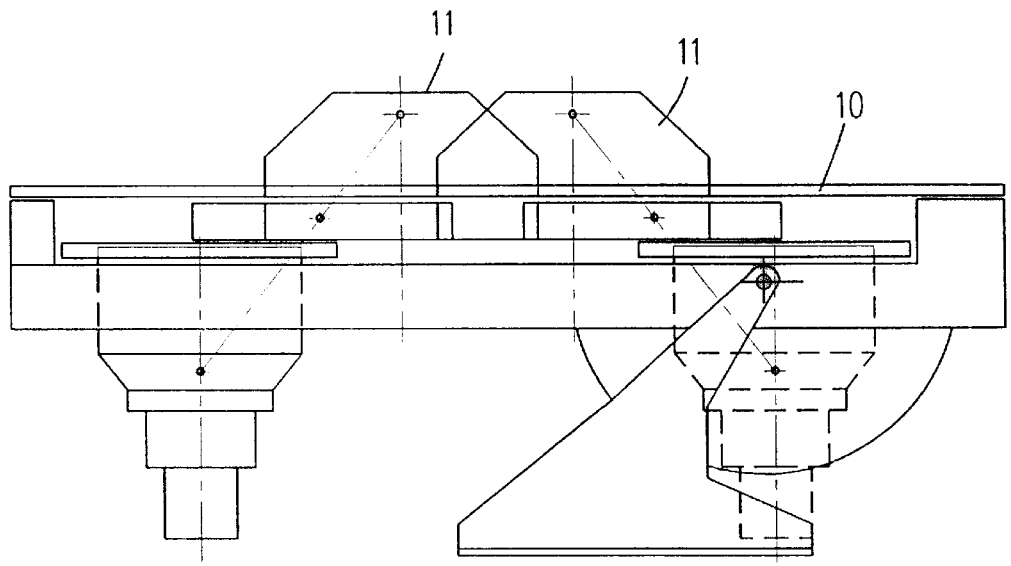
FIG. 7 shows the possibilities of movement of the apparatus for tomography.

FIG. 7 shows diagrammatically the circumstances for the apparatus shown in FIG. 1. It appears that for slice exposures the slice unit 11a can be moved to the positions at the head or the foot shown in FIG. 7 only while avoiding a collision between the image intensifier 7, or the carriage supporting it, and the crossbars 22 (FIG. 2) at the head end and the foot end of the patient table. Areas which are situated further at the head end or the foot end are not accessible for slice exposures; this is a drawback notably when, as specified, the table top 10 cannot be displaced relative to the frame.

Figure 9:
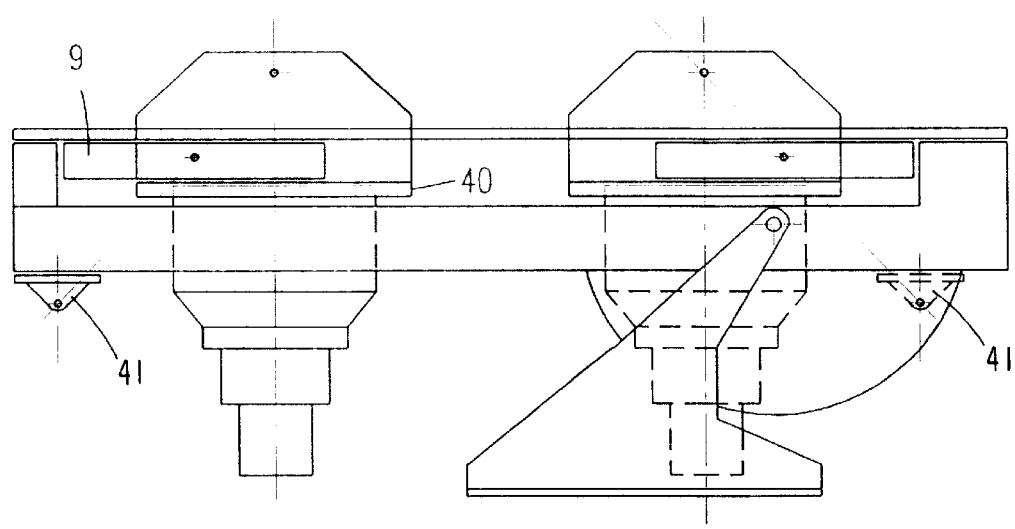
FIG. 9 shows the resultant range of movement for tomography.

FIG. 9, however, shows the circumstances in the embodiment shown in FIG. 8. It appears that the extreme positions at the head end and the foot end may be situated significantly further apart than in FIG. 7, because it is not necessary to move the voluminous image intensifier 7 and the carriage 40 supporting it, but only the comparatively narrow drive carriage 41 which is guided underneath the left-hand lower sleeper. The part of a patient that can be imaged by the slice exposures is thus significantly enlarged.

Figure 10:
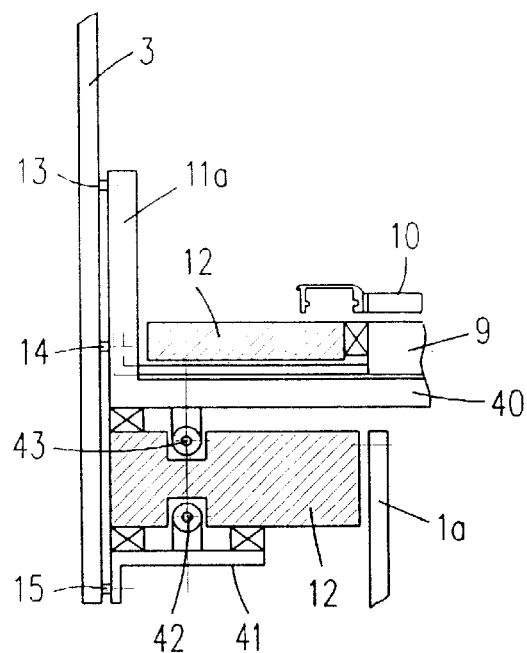
FIG. 10 is a partial front view of a further improved embodiment.

FIG. 10 shows an improvement of the embodiment shown in FIG. 8. The improvement consists in that the carriage 40 can be displaced via a spindle drive 43 (or a chain drive or a toothed rack). The following modes of operation are then possible.

In the first mode of operation, both the drive 42 for the carriage 41 and the drive 43 for the carriage 40 are activated in such a manner that the two carriages 40 and 41 are displaced in the direction of the head end or the foot end of the table at the same speed. The coupling member 3 is then displaced laterally and takes along the stand. In this mode of operation it is possible to perform Bucky exposures in conformity with FIG. 2 or X-ray fluoroscopy in conformity with FIG. 3, the X-ray source then being displaced parallel to the relevant longitudinal direction of the table.

In the second mode of operation, the spindle drive 43 is activated, i.e. the carriage 40 cannot be displaced relative to the sleeper 12, whereas the spindle drive 42 can act on the carriage 41. As a result, the coupling member 3 is pivoted about the pivot 13, and a slice exposure in conformity with FIG. 4 or FIG. 9 is performed.

The advantage of this embodiment resides in the fact that it is not necessary to lock the various carriages or the coupling member 3 to one another in dependence on the mode of operation, as in the embodiments shown in the FIGS. 1 and 8. Moreover, switching over between the two modes of operation is simply possible by means of switches provided in appropriate locations. A common drive motor may in principle be provided for the two spindle drives 42 and 43, said motor acting on the spindle drive 43 via a coupling which can be electrically activated and deactivated, since either the two drives operate in synchronism (first mode of operation) or only the drive 42 is activated (second mode of operation).

What is claimed is:

1. An X-ray examination apparatus which includes
a patient table which is tiltable about a horizontal axis,
an image converter arrangement which is displaceable in the longitudinal direction of the table,
an overtable X-ray source which is aligned with respect thereto,
a stand which is displaceable in the longitudinal direction of the table, and
wherein the X-ray source is mounted on the stand so as to be displaceable in the vertical direction and can be coupled, via a mechanical coupling member, to the patient table in such a manner that upon tilting of the patient table the stand and the X-ray source are displaced in such a manner that the distance between and the alignment of the image converter arrangement and the X-ray source with respect to one another remain the same.

2. An X-ray examination apparatus as claimed in claim 1, characterized in that the X-ray source is mounted on a horizontal arm which is tiltable about its central axis and is detachably connected to the coupling member.

3. An X-ray examination apparatus as claimed in claim 2, characterized in that the arm is connected to a carriage which is displaceable in the vertical direction on the stand.

4. An X-ray examination apparatus as claimed in claim 3, characterized in that the arm is connected to the carriage so as to be tiltable about a vertical axis.

5. An X-ray examination apparatus as claimed in claim 1 wherein there are provided coupling means whereby the coupling member establishes a rigid coupling between the X-ray source and the image converter arrangement in a first mode of operation and whereby the coupling member provides a displacement in opposite directions between the X-ray source and at least a part of the image converter arrangement in a second mode of operation, and wherein in the first mode of operation the rigidly-coupled X-ray source and image converter arrangement are displaceable as a unit in the longitudinal direction of the table.

6. An X-ray examination apparatus as claimed in claim 5, characterized in that the coupling member includes a unit for slice height adjustment which is coupled to a carriage which is displaceable in the longitudinal direction of the patient table, that the coupling member is hinged to the unit for adjusting the slice height at a coupling point whose height can be adjusted, and that the carriage can be displaced freely in the first mode of operation and is blocked relative to the patient table in the second mode of operation.

7. An X-ray examination apparatus as claimed in claim 6, characterized in that the patient table includes a drive device which acts on a carriage which is displaceable in the longitudinal direction of the patient table, and that the coupling member is coupled to this carriage at a distance from the coupling point.

8. An X-ray examination apparatus as claimed in claim 5, characterized in that the image converter arrangement includes a fluoroscopy image converter and an exposure image converter which are mounted on a respective carriage which is coupled to the coupling member and is displaceable in the longitudinal direction of the patient table.

9. An X-ray examination apparatus as claimed in claim 6 wherein the image converter arrangement includes a fluoroscopy image converter and an exposure image converter, wherein the fluoroscopy image converter and the unit for slice height adjustment are accommodated on a common carriage, wherein the patient table includes a first drive device which acts on a carriage which is displaceable in the longitudinal direction of the patient table, wherein the coupling member is coupled to this carriage at a distance from the coupling point, and wherein the coupling means couple the two carriages to one another in the first mode of operation and block the carriage with the fluoroscopy image converter relative to the patient table in the second mode of operation.

10. An X-ray examination apparatus as claimed in claim 9, characterized in that there is provided a second drive device which acts on the carriage with the fluoroscopy image converter, and that the two drive devices are controlled in such a manner that the two carriages are displaced at the same speed and in the same direction in the first mode of operation and that the second drive device is deactivated in the second mode of operation.

11. An X-ray examination apparatus as claimed in claim 8 further comprising a unit for slice height adjustment, and wherein the fluoroscopy image converter and the unit for slice height adjustment are accommodated on a common carriage, wherein the patient table includes a first drive device which acts on a carriage which is displaceable in the longitudinal direction of the patient table, wherein the coupling member is coupled to this carriage at a distance from the coupling point, and wherein the coupling means couple the two carriages to one another in the first mode of operation and block the carriage with the fluoroscopy image converter relative to the patient table in the second mode of operation.

\* \* \* \* \*